United States Patent [19]

McRae

[11] Plant 5,007

[45] Mar. 22, 1983

[54] LILY PLANT: LILIUM 'PICASSO'

[75] Inventor: Edward A. McRae, Boring, Oreg.

[73] Assignee: Melridge, Inc., Sandy, Oreg.

[21] Appl. No.: 200,969

[22] Filed: Oct. 27, 1980

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Eugene D. Farley

[57] ABSTRACT

A new variety of Asiatic hybrid lily plant bearing large clusters of medium-sized flowers of excellent form, unusual color, and long persistence, both on the plant and as cut flowers. The plant is characterized by rapid natural propagation under field conditions as well as by vigorous and healthy growth when forced under glass. The buds are brilliant orange. The flowers are brilliant orange, unspotted but characterized by the presence of distinctive oxblood red "brush marks".

1 Drawing Figure

BACKGROUND AND GENERAL STATEMENT OF THE INVENTION

Lilium 'Picasso' is classified botanically as a Lilium hybrid; commercially, as an upright Asiatic hybrid, Div. 1A in the Horticultural Classification of the Genus Lilium adopted by The Royal Horticultural Society of London.

It was discovered when it first flowered in 1970 among the seedling beds of test crosses of Oregon Bulb Farms, Sandy, Oreg. The cross was made in the year 1968.

The cross was made between the seed parent 'Enchantment' U.S. Plant Pat. No. 862 and the pollen parent 'Connecticut King' (unpatented).

The cross was made during a breeding program having for its objective the production of brilliantly-colored, upright flowering lily cultivars which would perform well when forced into flower under glass throughout the year, in addition to meeting the requirements of vigor, disease resistance, and rapid natural propagation under field cultivation. Cultivars were sought which would be disease resistant, virus tolerant, and not overly susceptible to leaf scorch and bud abortion upon forcing under glass.

My new lily plant resulting from this program is characterized by rapid natural propagation under field conditions as well as by vigorous and healthy growth when forced under glass. The buds are brilliant orange. The flowers are particularly distinctive in that they are brilliant orange, unspotted, but characterized by the presence of distinctive oxblood red "brush marks".

My new variety most closely resembles the older cultivar 'Enchantment', but differs from it and is superior to it because of its more intense flower color, its lack of spots, and the distinctive brush marks which add interest to the flowers.

My new variety of lily plant has been asexually reproduced by me and under my direction at Sandy, Oreg. Successive generations produced by bulb scale propagation and natural propagation from bulblets have demonstrated that the novel and distinctive characteristics of my new variety are fixed and hold true under asexual propagation from generation to generation.

THE DRAWING

My new variety of lily plant is illustrated in the accompanying photographic drawing which shows the plant, its foliage, its buds in their various stages of development, and the open bloom in full color.

DESCRIPTION OF THE NEW VARIETY

The following is a detailed description of my new variety of Asiatic hybrid lily, with nomenclature according to *The International Lily Register* (Royal Horticultural Society, London, 2nd edition, 1969) and with color designations according to The Royal Horticultural Society Color Chart, published by The Royal Horticultural Society in 1966.

THE PLANT

Form: Bulbous monocotyledon.

Height: 70–90 cm (28–36") from bulbs 15–18 cm in circumference.

Growth: Vigorous, with considerable strength.

Foliage: Abundant, about 80–100 leaves per stem.

*Size of leaves.*—6–9 cm (2½–3½") long and 1–2 cm (½–1") wide.

*Shape of leaves.*—Broad lanceolate.

*Texture of leaves.*—Leaves entire, not serrated, glossy, smooth, and glabrous.

*Color of leaves, upperside.*—Light glossy green.

*Color of leaves, underside.*—Light glossy green.

*Ribs and veins of leaves.*—Typical monocotyledonous venation: light green parallel veins.

Color of bulbs: White.

Size of bulbs: Usual commercial size is 12–20 cm (5–8") in circumference; bulbs can be cultivated for a longer time to reach much larger sizes if desired.

INFLORESCENCE

Compact raceme: Bulbs 12–15 cm in circumference produce about 7 buds.

No hairy peduncle or pedicels.

Strength of inflorescence: Strong and wirey.

Color of inflorescence: Stems are medium green overlaid with reddish anthocyanin pigment. Buds are brilliant orange.

THE BUD

Size: 7–9 cm (3–3½") long.

Form: Lanceolate with obtuse tip; typical of upright Asiatic hybrid lilies.

Opens slowly: Opens in about 1 hour in response to morning light; flowers which are further up the stem open on subsequent days over an interval of 1–2 weeks. Typical of upright Asiatic hybrid lilies.

Color of mature buds: Brilliant orange, R.H.S. CC #30B.

THE FLOWER

Blooms: Late June or early July in western Oregon, once, in midseason, and profusely.

Size:

*Flower diameter.*—15–18 cm (6–7").

*Inner tepals.*—3–4 cm (1¼–1½") wide.

*Outer tepals.*—2–3 cm (¾–1¼") wide.

Shape when flower first opens: Shallow bowl-shape with slightly recurving tepals.

Tepals recurve more as flower ages.

Tepal arrangement: Typical of the genus Lilium, with six entire, imbricated tepals.

*Color, outer tepal.*—Brilliant orange, Royal Horticultural Society of London's Color Code #30A, with a 2 cm-wide blotch of oxblood red (R.H.S. CC #59A) just above the nectaries.

*Color, base of tepals.*—Brilliant orange, R.H.S. CC #30A.

*Color, inner tepal.*—Brilliant orange, R.H.S. CC #30A at margins, 30 B-C in center, with a 2 cm-wide oxblood red blotch (R.H.S. CC #59A) at base.

*Color, reverse of tepals.*—Brilliant orange, R.H.S. CC #30A-B.

Tepals remain on individual flowers 5–7 days; stem has flowers with tepals adhering for about 3 weeks.

The illustrated color is less orange than the actual color, in view of the lighting condition at the time the blossoms were photographed. The variety, Enchantment shows the true orange color, but with less intensity.

Flower texture: Shiny, velvety. Not affected by hot or wet weather.

*Persistence.*—It does not hang on and dry; tepals fall as flower ages.

Pedicels: 5–10 cm (2–4"). Sturdy and upright.

*Color.*—Medium green, overlaid with light reddish anthocyanin pigment.

Disease resistance: to Botrytis blight and to Fusarium bulb rot.

Fragrance: None.

Lasting quality: Flowers remain on plants for about 3 to 4 weeks. Flowers remain on cut-flower stems for about 3 weeks, with adequate light.

REPRODUCTIVE ORGANS

Stamens and anthers: Typical of genus Lilium. Six versatile anthers hang (singly) from 6 filaments.

Filaments: 5–6 cm (2") long and light orange.

Pollen: Brilliant orange, R.H.S. CC #30B-C.

Pistil: 1, typical of genus Lilium. Stile is 5–6 cm (2") long.

Stigma: Small, 3-lobed, soft buff-orange in color, velvety in texture.

Ovary: Typical of genus Lilium. Superior, 6-chambered, single ovary.

THE FRUIT

Fertile, an ovoid to oblong capsule with 6 chambers.

Color at maturity: Medium green overlaid (under cool conditions) with light purple; fades to soft brown when capsule splits open to release seeds.

I claim:

1. A new and distinctive variety of Asiatic hybrid lily plant substantially as shown and described, characterized by its rapid natural propagation under field conditions, by its vigorous and healthy growth when forced under glass, by the brilliant orange color of its buds, and by its brilliant orange flowers, unspotted but characterized by the presence of distinctive oxblood red "brush marks".

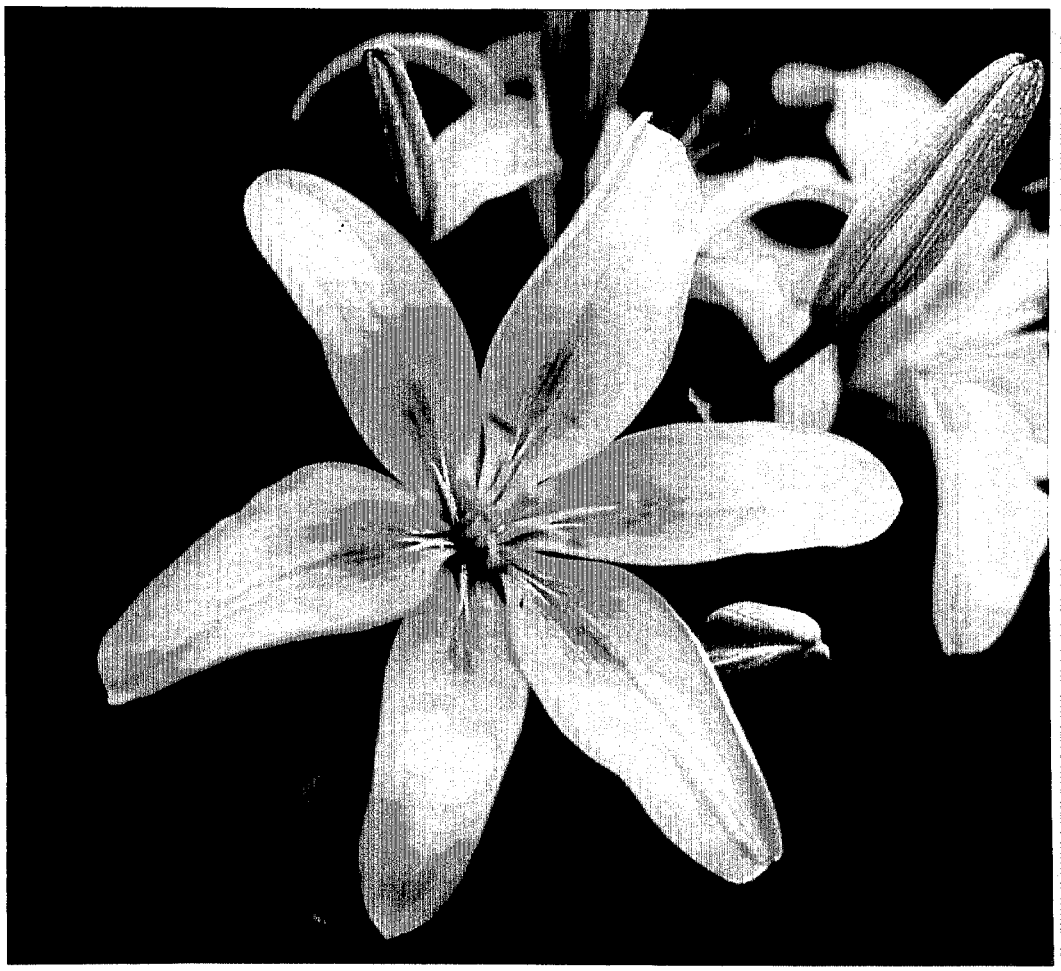

* * * * *